United States Patent
Henriksson et al.

(10) Patent No.: US 9,243,078 B2
(45) Date of Patent: Jan. 26, 2016

(54) METHOD TO INCREASE THE MOLECULAR WEIGHT OF WOOD MANNANS AND XYLANS COMPRISING AROMATIC MOIETIES

(75) Inventors: Gunnar Henriksson, Solna (SE); Dimitri Areskogh, Nacka (SE); Petri Oinonen, Stockholm (SE)

(73) Assignee: Ecohelix AB, Hagersten (SE)

( * ) Notice: Subject to any disclaimer, the term of this patent is extended or adjusted under 35 U.S.C. 154(b) by 36 days.

(21) Appl. No.: 13/988,861

(22) PCT Filed: Nov. 23, 2011

(86) PCT No.: PCT/SE2011/051405
§ 371 (c)(1),
(2), (4) Date: Jun. 27, 2013

(87) PCT Pub. No.: WO2012/071004
PCT Pub. Date: May 31, 2012

(65) Prior Publication Data
US 2013/0289255 A1    Oct. 31, 2013

Related U.S. Application Data

(60) Provisional application No. 61/416,326, filed on Nov. 23, 2010.

(30) Foreign Application Priority Data

Nov. 23, 2010   (SE) ..................... 1051224

(51) Int. Cl.
| C08B 37/00 | (2006.01) |
| C08H 8/00 | (2010.01) |
| C12P 19/04 | (2006.01) |
| C08B 37/14 | (2006.01) |
| C08H 7/00 | (2011.01) |

(52) U.S. Cl.
CPC ........... *C08B 37/143* (2013.01); *C08B 37/0003* (2013.01); *C08B 37/0057* (2013.01); *C08B 37/146* (2013.01); *C08H 6/00* (2013.01); *C08H 8/00* (2013.01); *C12P 19/04* (2013.01); *C12Y 110/03002* (2013.01); *C12Y 111/01* (2013.01)

(58) Field of Classification Search
CPC ........ C08B 37/0057; C08H 8/00; C12P 19/04
See application file for complete search history.

(56) References Cited

U.S. PATENT DOCUMENTS

| 5,505,772 A | 4/1996 | Kharazipour et al. |
| 5,530,112 A * | 6/1996 | Greenshields et al. .... 536/123.1 |
| 5,846,788 A | 12/1998 | Pedersen et al. |
| 5,998,176 A * | 12/1999 | Budolfsen et al. ............ 435/101 |
| 6,033,712 A * | 3/2000 | Greenshields et al. ........ 426/573 |
| 6,087,135 A * | 7/2000 | Kierulff ......................... 435/101 |
| 6,174,549 B1 | 1/2001 | Greenshields et al. |
| 6,232,101 B1 | 5/2001 | Budolfsen et al. |
| 6,346,401 B1 * | 2/2002 | Kierulff ......................... 435/101 |
| 8,377,670 B2 * | 2/2013 | Kerovuo et al. .............. 435/189 |
| 8,603,787 B2 * | 12/2013 | Medoff .......................... 435/165 |
| 2001/0055794 A1 * | 12/2001 | Kierulff ......................... 435/101 |
| 2006/0128952 A1 * | 6/2006 | Schroder et al. .............. 536/123 |
| 2009/0075845 A1 * | 3/2009 | Abad et al. .................... 507/117 |
| 2009/0311752 A1 | 12/2009 | Bodie |
| 2010/0129642 A1 * | 5/2010 | Grondahl et al. ............. 428/324 |
| 2011/0005697 A1 * | 1/2011 | Shoseyov ...................... 162/174 |
| 2011/0294925 A1 * | 12/2011 | Shaler et al. .................... 524/14 |
| 2012/0107886 A1 * | 5/2012 | Albizati et al. ............... 435/146 |
| 2013/0101699 A1 * | 4/2013 | Lacaze et al. ................... 426/31 |

FOREIGN PATENT DOCUMENTS

| WO | 9717492 | 5/1997 |
| WO | 03047826 | 6/2003 |
| WO | 2004083256 | 9/2004 |
| WO | WO 2008103123 A2 * | 8/2008 |

OTHER PUBLICATIONS

Hamid et al. (Food Chemistry 115, 2008, 1177-1186).*
Ebringerova et al. (Macromol. Rapid Commun. 21, 542-556, 2000.*
Oosterveld, Formation of Feulic Acid Dehydrodimers Through Oxidative Cross-Linking of Sugar Beet Pectic, Carbohydrate Research 300 (1997), 179-181.
Written Opinion for PCT/SE2011/051045 mailed Mar. 6, 2012.
International Search Report for PCT/SE2011/051045 mailed Mar. 6, 2012.

* cited by examiner

*Primary Examiner* — Liam J Heincer
(74) *Attorney, Agent, or Firm* — Gabriela B. Tomescu, Esq.; Bergenstrahle & Partners Stockholm AB

(57) ABSTRACT

A method to increase the molecular weight of wood mannans and xylans comprising aromatic moieties comprises the steps: a) obtaining mannan and/or xylan from wood, b) subjecting the mannan/xylan to oxidizing conditions to convert at least a fraction of the aromatic groups into radicals and reacting said radicals with each other to obtain complexes of mannan/xylan with increased molecular weight. The method is easy and cost efficient and enables to upgrade small wood mannans and xylans that are important in the pulp and paper industry into larger mannans and xylans and more defined structures which makes their isolation easier and application areas broader. Another advantage is that separation of mannans and xylans from mannans and xylans with bound aromatic groups is provided. The wood mannans and xylans with increased molecular weight can be used for the manufacture of barrier films in packages, for instance for oxygen, liquids and gas.

10 Claims, 2 Drawing Sheets

METHOD TO INCREASE THE MOLECULAR WEIGHT OF WOOD MANNANS AND XYLANS COMPRISING AROMATIC MOIETIES

CROSS-REFERENCE TO RELATED APPLICATIONS

This application is the U.S. national phase entry of PCT/SE2011/051405, with an international filing date of 23 Nov. 2011, which claims the benefit of Swedish patent application no. 1051224-2, with a filing date of 23 Nov. 2010 and U.S. patent application No. 61/416,326, with a filing date of 23 Nov. 2010, the entire disclosures of which are fully incorporated herein by reference.

TECHNICAL FIELD

The present invention relates generally to the crosslinking and processing of wood mannans and xylans with bound aromatic moieties.

BACKGROUND ART

The increasing cost pressure in the pulping and other biomass utilizing industry as well as the increasing awareness of the problems related to fossil oil based products has led to the search of new renewable raw materials for energy and material applications. The use of for example renewable and easily degradable packaging films or fuels produced from wood sugars could result in significant decreases of the carbon footprint of these industries. Today's pulping processes give rise to discharges of oxygen demanding substances, which are normally taken care of in biological purification of the outlet water. It is costly to build such purification plants.

Lignocellulosic materials are complex structures consisting of a multitude of different kind of molecules that are bound to one another with chemical bonds. This causes significant problems in the fractionation, upgrading and the use of the molecules. There is no broad consensus among researchers about the existence of natural covalent bonds between lignin and hemicelluloses in wood. An often used view is that these bonds are formed during the processing of the molecules. Some new research data however have suggested that aromatic structures are covalently bound to cellulose and hemicelluloses through ester-, ether- or phenyl glucosidic bonds. This was reported by for example Iawoko and coworkers, Holzforschung, Vol 60, pp. 156-161, 2006.

Two types of phenolic polysaccharides are well known and characterized. Ferulated arabinoxylans have ferulic acid moieties attached to the polysaccharides and they are known to be present in grasses and cereals. Phenolic pectins can be found i.e. from beet pulp. It is also known that polysaccharides can be derivatized with e.g. aromatic compounds.

Barrier films are used in packaging to increase the shelf life of the product by keeping it away from odors, oxygen gas etc. Petroleum based and aluminum films are dominating the field but films made of renewable materials have gained a lot of interest in latest years. Starch based films are the most widely applied renewable polymers for this purpose but they are based on food based resources.

Different branched and non-branched polysaccharides (including but not limited to hemicelluloses) are together with lignin and cellulose the main constituents of wood (as well as many other lignocellulosic materials). They have been shown great potential as raw material for material and chemical applications as well as a feedstock for fermentations. Wood hemicelluloses such as mannans and xylans can be isolated from the process waters of mechanical pulping or from a pre-hydro lysis process with a price that is competitive with the petrochemical based equivalents. Considering the large size of this industry worldwide, it can be said that these hemicelluloses are available in great amounts, further advantages for the use of this raw material source include the renewable nature of the material as well as the fact that this material source is not part of the food production. Drawbacks of the hemicelluloses derived from these processes are that their molecular weight is very low and they exist in complex mixtures with other compounds in the process waters.

The international patent application WO 97/17492 describes a way to prepare a pulp strengthening agent and its addition to a lignocellulosic product. The lignocellulosic fiber product can be paper and paperboard originating from wood, flax, cotton, hemp, jute and bagasse and can be achieved through different pulping processes. The strengthening agent is achieved through treating a phenolic polysaccharide obtained from potato, corn, waxy corn, wheat, rice, sorghum, waxy sorghum, sago arrowroot or tapioca with an oxidizing agent that catalyzes the oxidation of the phenolic groups. The patent publication discloses in more detail the following types of polysaccharides that could possibly be applied: a) The phenolic polysaccharides such as phenolic starches and phenolic cationic starches are achieved through derivatization of the "parent starch", b) Phenolic celluloses into which phenolic substituents has been introduced, c) Phenolic polysaccharides derived from polysaccharides of the following types: pectins, galactomannans (guar gum or locust bean gum), arabinogalactan (from western larch timber), dextrans, acacia gum, xanthan gum, tragacanth gum and carrageenan. The phenolic polysaccharides disclosed in this publication are not obtained from wood tissues that are important in the pulp and paper industry, but mostly from cereal crops (monocotyledons) used in the food industry. Xylans and mannans obtained from wood (conifers and eudicotyledons) are not described. The patent application does not describe the use of the polysaccharides in barrier film production.

The U.S. Pat. No. 6,232,101 describes a method for the production of a gelling agent for aqueous liquids for foodstuff, medical/medicinal or agricultural/horticultural applications intended for ingestion. The polysaccharide that contains phenolic hydroxyl groups intended for this application is obtainable from cereals (e.g. hemicelluloses from wheat or maize flour or bran) or from a plant that is a member of the family Cheniopodiaceae (e.g. pectins from sugar beet pulp). The phenolic hydroxyl groups are oxidized and the gelling phenomenon occurs. The produced material can exhibit excellent liquid-absorption and liquid-retention properties. The use of wood derived polysaccharides is not described nor is the use of the pro duct for material applications.

The international patent application WO2004/083256 teaches how to prepare food products, such as emulsions and foams by covalently linking combinations of a protein, a glyceride and a polysaccharide that contain covalently bonded phenolic residues. The polysaccharides (arabinoxylans and pectins) are obtained from sugar beet and cereals and they were thoroughly described by Lex Oosterveld, Carbohydrate research 300, 179-181, 1997 and thesis Lex Oosterveld, Landbouwuniversiteit Wageningen Netherlands, Dec. 15, 1997, ISBN 90-5485785-4. It is to be noted that these polysaccharides are obtainable from cereals and sugar beets and not from wood and the application areas does not include material applications.

US patent application US2009311752 describes a technique for treating hydrolysates of lignocellulosic biomass with phenol oxidizing enzymes such as laccase in order to enhance growth of microorganisms that are sensitive to the inhibitory compounds in the biomass originating from lignin. There is disclosed the neutralization of monomeric, phenolic inhibitory compounds by, for instance, laccase treatment in the lignocellulose biomass after hydrolysis.

In general the documents reviewed above describes the use of the phenolic polysaccharides in the preparation of strengthening agents for pulp, gelling agents, medical/medicinal or agricultural/horticultural applications, emulsions and foams but not for the preparation of material products for i.e. packaging applications, neither is described the purification of polysaccharides from a mixed solution by utilizing the crosslinking method. Even more importantly the described polysaccharides in the above mentioned publications are mostly obtained from various agricultural crops (such as ferulated arabinoxylans, pectins and aromatic starches) that are well known to contain bound aromatic moieties. Wood hemicelluloses (mannans and xylans) and especially those derived from the process waters of pulping processes are not described.

In the prior art there is still a need to solve the problem with industrial production of high molecular weight mannans and xylans derived from wood (that are not derivatized). In the prior art there is also the problem with contamination of hemicelluloses by lignin. In the prior art there is further a problem how to separate mixtures of hemicelluloses with and without bound aroma tics groups.

SUMMARY OF INVENTION

It is an objective of the present invention to obviate at least some of the disadvantages in the prior art and to provide a method for upgrading mixtures of wood hemicelluloses wherein the hemicelluloses are selected from mannans and xylans.

In a first aspect there is provided a method for increasing the molecular weight of hemicellulose selected from the group consisting of mannan and xylan, said method comprising the steps:

a) obtaining at least one hemicellulose, wherein the hemicellulose is selected from the group consisting of mannan and xylan from wood, said hemicellulose comprising at least one bound aromatic group, b) subjecting the hemicellulose to oxidizing conditions to convert at least a fraction of said at least one aromatic group into radicals and reacting said radicals with each other to obtain complexes of hemicelluloses with increased molecular weight.

In a second aspect there is provided a hemicellulose obtained from wood wherein the hemicellulose is selected from the group consisting of mannan and xylan, which hemicellulose has been subjected to a chemical reaction to increase its molecular weight, the hemicellulose comprising at least one bound aromatic group, wherein at least a fraction of said bound aromatic groups are covalently bound to each other.

In further aspects there are provided barrier films comprising the hemicellulose with increased molecular weight for various applications such as a barrier film, an oxygen barrier film, a liquid barrier film, and a fat barrier film.

In still further aspects there are provided use of a hemicellulose with increased molecular weight for the manufacture of a barrier film in a package, a packaging material, a barrier material, an oxygen barrier material, a liquid barrier material, and a fat barrier material.

Further aspects and embodiments are defined in the appended claims, which are specifically incorporated herein by reference.

One advantage of the invention is that it provides an easy and cost efficient technique that enables to upgrade small wood hemicelluloses into larger and more defined structures which makes their isolation easier and application areas more broad.

Another advantage is that separation of wood hemicelluloses from wood hemicelluloses with bound aromatic groups is provided.

As a conclusion it can be stated that by using the oxidative treatment, surprisingly it was possible to increase the molecular weight of the mannans and xylans obtained from wood. This has never been described for these hemicelluloses before. This makes possible to utilize pulp and paper industry derived hemicelluloses in material applications that earlier was difficult because of the low molecular weight and contamination with lignin. It is important to notice that this makes possible to utilize a totally new raw material source that is renewable, is not part of the food production, is originating from wood material including but not limited to Norway spruce and Eucalyptus (among other wood species) that are important for the pulp and paper industry. This is expected to make it easier to process the pulp and paper industry process derived hemicelluloses and significantly improve the profitability of bio refinery concepts that are currently being introduced to the pulp and paper industry. Furthermore the invention makes it possible to use the described renewable wood hemicelluloses for packaging applications instead of petroleum based plastics or aluminum thus making the carbon foot print of these products significantly smaller. Additionally the technique makes it easier to use the hemicelluloses in fermentation applications.

The raw material is available in large quantities at low cost.
The energy consumption during manufacture is low.
The material is bio degradable.
Addition of aromatic groups is not necessary.

BRIEF DESCRIPTION OF DRAWINGS

The invention is described, by way of example, with reference to the accompanying drawing, in which.

DETAILED DESCRIPTION

Figure 1:
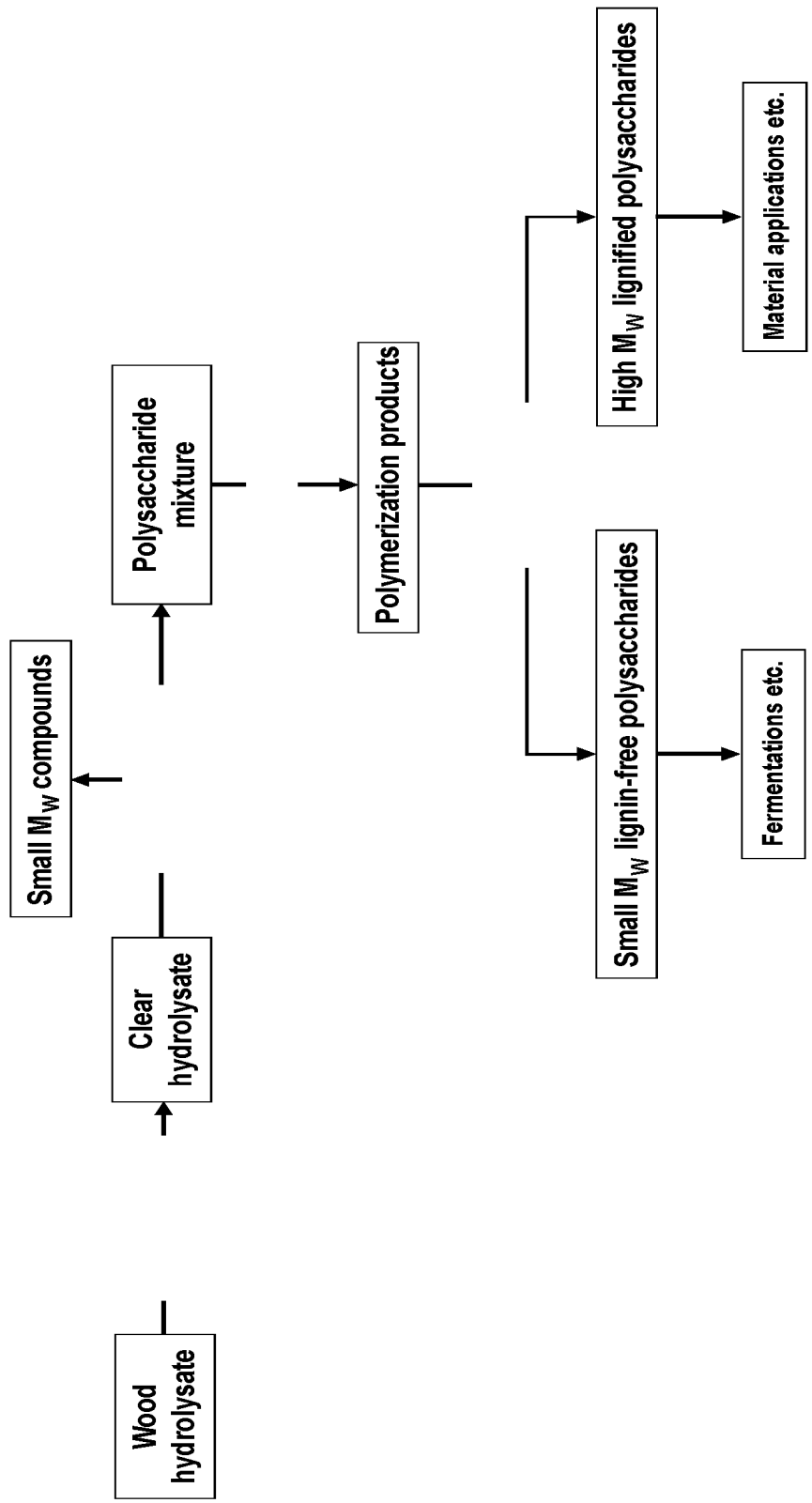
FIG. 1 shows a schematic view of one embodiment of the invention.

Before the invention is disclosed and described in detail, it is to be understood that this invention is not limited to particular compounds, configurations, method steps, substrates, and materials disclosed herein as such compounds, configurations, method steps, substrates, and materials may vary somewhat. It is also to be understood that the terminology employed herein is used for the purpose of describing particular embodiments only and is not intended to be limiting since the scope of the present invention is limited only by the appended claims and equivalents thereof.

It must be noted that, as used in this specification and the appended claims, the singular forms "a", "an" and "the" include plural referents unless the context clearly dictates otherwise.

If nothing else is defined, any terms and scientific terminology used herein are intended to have the meanings commonly understood by those of skill in the art to which this invention pertains.

The term "about" as used in connection with a numerical value throughout the description and the claims denotes an interval of accuracy, familiar and acceptable to a person skilled in the art. Said interval is ±10%.

"Bound" is used herein to denote that a chemical group is bound by a chemical bond. Chemical bonds include covalent bonds, ionic bonds, dipole-dipole interactions, London dispersion forces and hydrogen bonding.

"Plants" is used herein to denote living organisms belonging to the kingdom Plantae. The term includes, but is not limited to trees, herbs, bushes, grasses, ferns, mosses and green algae.

"Polysaccharide" is used herein to denote polymeric carbohydrate structures, formed of anhydrous monosaccharides joined together by glycosidic bonds. A "heteropolysaccharide" is a polysaccharide with two or more different mono saccharide units. A "homopolysaccharide" is a polysaccharide with one type of monosaccharide unit "Hemicellulose" is a cell wall polysaccharide of land plants with an amorphous structure. "Wood hemicellulose" is a polysaccharide found in softwoods (conifers) and hardwoods (eudicotyledons).

In a first aspect there is provided a method for increasing the molecular weight of hemicellulose selected from the group consisting of mannan and xylan, said method comprising the steps:

a) obtaining at least one hemicellulose, wherein the hemicellulose is selected from the group consisting of mannan and xylan from wood, said hemicellulose comprising at least one bound aromatic group, b) subjecting the hemicellulose to oxidizing conditions to convert at least a fraction of said at least one aromatic group into radicals and reacting said radicals with each other to obtain complexes of hemicelluloses with increased molecular weight.

The process through which reaction of the hemicelluloses occurs is based on oxidation of the aromatic moiety bound to the hemicellulose. Without wishing to be bound by any specific scientific theory the inventors speculate that during the oxidation, phenoxy radicals are formed. The radicals couple to each other and the molecular weight of the hemicellulose polymer increases. The hemicelluloses that do not contain bound aromatic moieties are not reacted or not reacted to any significant extent by the oxidative treatment and can therefore be separated based on molecular size, for instance separation with respect to molecular weight.

Examples of a hemicellulose include but are not limited to xyloglucan, xylan and mannan (including arabinoglucuronoxylan, glucuronoxylan, glucomannan and galactoglucomannan). In one embodiment the hemicellulose is at least one selected from the group consisting of arabinoglucuronoxylan, glucuronoxylan, glucomannan and galactoglucomannan.

In one embodiment the hemicellulose is a lignocellulose based hemicellulose, i.e. it is derived from an organism comprising lignin, hemicellulose and cellulose. Lignocellulose is biomass comprising cellulose, hemicelluloses and lignin. Lignocellulose is present in wood.

In one embodiment the mannan and/or xylan is obtained from a softwood species such as: Norway spruce (*Picea abies*), Engelmann spruce (*Picea engelmannii*), Black spruce (*Picea mariana*), White spruce (*Picea glauca*), Sitka spruce (*Picea sitchensis*), Western Hemlock (*Tsuga heterotallica*), Douglas fir (*Pseudotsuga menzisii*), Western redcedar (*Thuja pliceta*), Redwood (*Sequoia sempervirens*), Scots pine (*Pinus sylvestris*), Black pine (*Pinus nigra*), Aleppo pine (*Pinus halepensis*), Contorta pine (*Pinus contorta*), Weymouth pine (*Pinus strobes*), Slash pine (*Pinus elliotti*), Caribbean pine (*Pinus caribiae*) or Monterey pine (*Pinus radiata*).

In one embodiment the mannan and/or xylan is obtained from a hardwood species such as: Eucalyptus (*Eucalyptus grandis, Eucalyptus urograndis*, and *Eucalyptus globulus*), Acacia (*Acacia melanoxylon, Acacia homalophylla* and *Acacia magnium*), Birch (*Betula pendula*), Aspen (*Bopulus tremula*), Beech (*Fagus sylvatica*), Maple (*Acer campestre, Acer platanoides*), Poplar (*Populus balsamifera, Populus fremontii* and *Populus nigra*) or Oak (*Quereus* spp.).

In one embodiment the bound aromatic groups are lignin. Lignin comprises three different kinds of monomers; p-coumaryl alcohol, coniferyl alcohol, and sinapyl alcohol. Thus lignin comprises aromatic compounds which occur in at least one of the following plant-bio synthetic pathways: from p-coumaric acid to p-coumaryl alcohol, from p-coumaric acid to coniferyl alcohol and from p-coumaric acid to sinapyl alcohol; p-coumaric acid itself and the three mentioned end products of the latter three bio synthetic pathways.

In one embodiment the hemicelluloses comprising at least one bound aromatic group are those in which the aromatic group of the hemicellulose is a substituent derived from an aromatic compound which occurs in at least one of the following plant-bio synthetic pathways: from p-coumaric acid to p-coumaryl alcohol, from p-coumaric acid to coniferyl alcohol and from p-coumaric acid to sinapyl alcohol; p-coumaric acid itself and the three mentioned end products of the latter three biosynthetic pathways are also relevant compounds in this respect Examples of relevant intermediate compounds formed in these biosynthetic pathways include but are not limited to caffeic acid, ferulic acid (i.e. 4-hydroxy-3-methoxycinnamic acid), 5-hydroxy-ferulic acid and sinapic acid.

In one embodiment the hemicellulose comprising bound aromatic groups are provided in a mixture of hemicellulose with and without bound aromatic groups.

In one embodiment the mannan or xylan comprising bound aromatic groups are provided by hydro thermal treatment of wood.

In one embodiment the mannan or xylan comprising bound aromatic groups are provided by mechanical pulping. In one embodiment the hemicellulose comprising bound aromatic groups are provided by pre-hydrolysis pulping.

In one embodiment the mannan or xylan comprising bound aromatic groups are provided in an aqueous solution.

In one embodiment low molecular weight substances are removed from the hemicellulose mixture with at least one ultrafiltration membrane that has a cut-off between 1000 and 15000 Da preferably between 1000 and 5000 Da before step a). In one embodiment the cutoff is 1000 Da, in an alternative embodiment the cutoff is 5000 Da.

In one embodiment the pH is adjusted to a value in the range between 3 and 10, preferably between 5 and 7 before step a). The pH is preferably chosen according to the optimum of the oxidation tool to be employed.

In one embodiment the oxidation is achieved by adding an enzyme to the hemicellulose. In one embodiment the enzyme is an oxidoreductase. In one embodiment the enzyme is an oxidoreductase with oxygen as acceptor, preferably laccase. In one embodiment oxygen is added to the hemicellulose. Some enzymes require an oxidant to function optimally.

In one embodiment the enzyme is an oxidoreductase-acting on peroxide as an acceptor, preferably a peroxidase. In one embodiment hydrogen peroxide is added to the hemicellulose.

In one embodiment involving enzymes the temperature is in the range from 20 to 80° C., preferably between 30 to 60° C. The temperature is preferably chosen according to the optimum of the oxidation tool to be employed.

In one embodiment the enzyme is immobilized on a support. An immobilized enzyme is covalently bound to a support Examples of a support include but are not limited to a reaction tank, and particles. The immobilization of an enzyme provides advantages regarding for instance economy since less enzyme is used. Any suitable enzyme can be immobilized. In one embodiment laccase is immobilized.

In one embodiment the oxidation is achieved by adding a chemical oxidant to the hemicellulose.

In one embodiment the enzyme which is used for polymerization is covalently bound to a solid support, i.e., immobilized.

In one embodiment the resulting compounds are subjected to a derivatization step. In one embodiment the derivatization comprises acetylation. In one embodiment the acetylated products are filtered afterwards.

If the starting material comprises hemicellulose both with and without bound aromatic groups, fractions are formed as a consequence of the radical cross linking; a high-molecular-weight fraction and a non-cross linked hemicellulose fraction. The two fractions can be separated by means of physical separation including but not limited to filtration and size exclusion chromatography. In one embodiment the resulting compounds are subjected to a separation with respect to molecular weight. This has the advantage of providing a possibility to separate hemicellulose comprising bound aromatic groups from hemicelluloses without bound aromatic groups, since the hemicellulose comprising bound aromatic groups will polymerize giving an increased molecular weight. Thus it is possible to utilize the different fractions for further use.

In one embodiment the resulting hemicelluloses with increased molecular weight are subjected to at least one selected from ultrafiltration and chromatography. In one embodiment the resulting hemicelluloses with increased molecular weight are subjected to at least one selected from cross flow ultrafiltration and size exclusion chromatography.

In one embodiment the process comprises three stages; extraction of hemicellulose from wood, oxidative reaction of the hemicellulose and separation of the fractions.

The extraction process is in one embodiment hydro thermal treatment of wood in neutral, slightly alkaline or slightly acidic conditions where water soluble hemicelluloses are extracted. TMP (thermomechanical pulping), CTMP (chemithermomechanical pulping) and pre-hydro lysis pulping are considered as such processes, because of similar process conditions. The extract is in one embodiment filtered (for instance by crossbow micro filtration) to achieve a clear solution. The extract is in one embodiment subjected to crossbow ultrafiltration with a small molecular weight (Mw) cut-off membrane (with a cut of value in the range from 1000 to 15000 Da) for the removal of low molecular weight substances and for increasing the concentration of the hemicelluloses to a certain concentration. The following reaction of the hemicelluloses is in one embodiment preceded by adjustment of the pH of the solution to between 3 and 10 by sodium hydroxide or sulfuric acid.

The enzymatic reaction of hemicelluloses comprising aromatic groups is in one embodiment achieved by adding enzyme to the solution and subjecting it to mixing and oxygen gas (or hydrogen peroxide) in a temperature between 20-80° C. The chemical reaction is achieved by adding a chemical oxidant to the hemicellulose solution. The reacted high molecular weight hemicelluloses are in one embodiment separated from the non-reacted, non-lignin (non-aromatic group) containing hemicelluloses based on their molecular weight.

In one embodiment bio chemical or chemical conversion is used for further converting the produced hemicellulose product to other products. In one embodiment the biochemical or chemical conversion is fermentation.

In one embodiment at least two different kinds of hemicelluloses are provided. Thus there is provided the possibility to manufacture reacted products comprising several different hemicelluloses.

In a second aspect there is provided a hemicellulose obtained from wood which has been subjected to a chemical reaction to increase its molecular weight, the hemicellulose comprising at least one bound aromatic group, wherein at least a fraction of said bound aromatic groups are covalently bound to each other.

In one embodiment the reacted hemicellulose with increased molecular weight is a constituent in a layer in a package (such as film or coating) for example a barrier for oxygen gas.

In one embodiment the hemicellulose obtained from wood is a constituent in a barrier film layer in a package.

There is provided a barrier film comprising a hemicellulose with increased molecular weight. There is provided a liquid barrier film comprising a hemicellulose with increased molecular weight. There is provided a fat barrier film comprising a hemicellulose with increased molecular weight. There is provided an oxygen barrier film comprising a hemicellulose with increased molecular weight.

There is provided use of a hemicellulose with increased molecular weight for the manufacture of a barrier film in a package. There is provided use of a hemicellulose with increased molecular weight for the manufacture of a packaging material. There is provided use of a hemicellulose with increased molecular weight for the manufacture of a barrier material. There is provided use of a hemicellulose with increased molecular weight for the manufacture of an oxygen barrier material. There is provided use of a hemicellulose with increased molecular weight for the manufacture of a liquid barrier material. There is provided use of a hemicellulose with increased molecular weight for the manufacture of a fat barrier material. The barrier materials are suitably utilized to manufacture barrier layer(s) in packages.

There is provided coatings and packages comprising several layers of hemicelluloses with increased molecular weight.

Possible products areas for the hemicelluloses with increased molecular weight include but are not limited to: anti-tumor drugs, anti-HIV drugs, drug delivery systems, biocompatible coatings, tissue engineering, scaffolds, nanocomposites, matrix systems, compatibilisers, impact strength modifiers, barrier coatings, fiber surface treatment, wet strength resin, filler replacements, novel fibers, super absorbents, hydrogels, water purifiers and chromatographic materials.

Spruce hemicelluloses can further be used for applications including but not limited to: specialty paper grades, abrasion-resistant clothing, antibacterial bandage, barriers against oxygen gas, water vapor or fat barriers in food pack, plant growth regulators, health-promoting agents (such as prebiotic substances), pharmaceuticals, emulsion stabilization in food and feed, emulsion stabilization and control of viscosity in cosmetic and selected technical applications and hydrogels.

The large molecular weight of the fraction that is achieved through the method opens new application areas for these hemicelluloses. One application area of the high molecular weight fraction is the oxygen barrier film applications. This application has been tested in the experimental part of the application. One application area of the small molecular weight fractions are the fermentation applications.

The hemicelluloses are in various embodiments provided by a process selected from TMP (thermomechanical pulping), CTMP (chemithermomechanical pulping) and pre-hydrolysis pulping processes. The hemicelluloses produced in these processes are produced in large scale, the technology can be applied to these processes with great ease and the hemicelluloses from these processes are currently without much commercial applications.

Other features and uses of the invention and their associated advantages will be evident to a person skilled in the art upon reading the description and the examples. Thus a skilled person realizes in the light of this description that it is possible to apply the technique to any kind of wood hemicellulose with a bound aromatic moiety regardless of what kind of process it is derived from, as long as it is derived from wood. Chemical pulping processes (namely the pulping liquors that contain wood hemicelluloses) including kraft, sulphite and soda processes are examples of such processes.

It is to be understood that this invention is not limited to the particular embodiments shown here. The following examples are provided for illustrative purposes and are not intended to limit the scope of the invention since the scope of the present invention is limited only by the appended claims and equivalents thereof.

EXAMPLES

The Analysis Methods
Carbohydrate and Lignin Analysis

The carbohydrate and lignin compositions of the samples were determined by employing the hydrolysis conditions described in the TAPPI-standard method (T249 cm-00, Carbohydrate Composition of Extractive-Free Wood and Wood Pulp by Gas Chromatography. Atlanta, TAPPI Press) with a slight modification in the acetylation stage which is described by Theander and Westerlund, 1986. (Theander, O., Westerlund, E. A. (1986) Studies on dietary fiber. 3. Improved procedures for analysis of dietary fiber. J. Agric. Food Chem. 34, 330-336. The mono sugar analyses were performed with a HP 6890 series gas chromatography device with a BP-70 column (60 m, 0.32 µm I.D., and 0.25 µm film thickness).

Ash Content

The ash content of the samples was measured according to the TAPPI-standard method (T211 om-85, Ash in wood and pulp, Atlanta, TAPPI Press).

SEC, Molecular Weight

The samples were analyzed using a size exclusion chromatography system consisting of a Rheodyne 7725i (Rohnert Park, Calif., USA) manual injector, a Waters 515 HPLC pump (Milford, Mass., USA) and three TSK-gel columns (Tosoh Bioscience, Tokyo, Japan) coupled in series, G3000PW (7.5× 300 mm, 10 µm particle size), G4000PW (7.5×300 mm, 17 µm particle size) and G3000PW. For detection, a Waters 2487 dual wavelength absorbance detector (Milford, Mass., USA) and a Waters 410 Refractive Index (RI) detector (Milford, Mass., USA) were used. The eluent system utilized was 10 mM sodium hydroxide made in ultra-pure laboratory grade Milli-Q water. A volume of 20 µl was injected, and the UV absorbance at 280 and 254 nm and RI detection was recorded. The columns were calibrated with polyethylene glycol (PEG) and polyethylene oxide (PEO) standards with specific molecular weights ranging from 1500 to 400 000. The integration and quantification of peaks were performed using the supplied Millennium 2 software.

Mechanical Properties

The mechanical properties of the films were tested according to the ASTM D882-09 standard (Standard Test Method for Tensile Properties of Thin Plastic Sheeting). The comparison of the stress-strain behavior of the films that gave a lesser mechanical strength (films with 60% sample polymer: SCHW UF1, SCHW UF1 P sMw, SCHW UF1 P HMw, TMP UF1, TMP UF1 P sMw, TMP UF1 P HMw) was determined using an Minimat 2000 (Rheometric Scientific) equipped with a 20 N load cell, and controlled by the Minimat software (Rheometric Scientific, version 2.4.6). The film with a higher mechanical strength (film made with 70% sample polymer TMP UF5 P HMw as well as the film made with 80% sample polymer CTMP UF5 P HMw) was determined using an Instron 5944-machine equipped with a 50 N load cell and controlled by the Bluehill 2 software (Instron). Films were cut into thin rectangular strips with a width of 5 mm and a gauge length of 15 mm. The stress-strain curves of specimen samples were recorded at room temperature and 50% RH at a strain rate of 10% $min^{-1}$. At least three specimens were tested from each sample and results were reported for those specimens that do not show premature failure at the jaw face. Stress-strain curves were plotted, and the Young's modulus (E) was determined from the slope of the low strain region in the vicinity of 0.05% strain.

Oxygen Permeability

The oxygen gas transmission rate of the films was measured using a Systech Instruments, 8001 oxygen permeation analyzer. Testing was performed at a temperature of 23° C., 50% relative humidity and one atmosphere oxygen pressure according to ASTM D3985 (Standard Test Method for Oxygen Gas Transmission Rate Through Plastic Film and Sheeting Using a Coulometric Sensor).

Fourier Transform Infrared Spectrometry

Fourier Transform Infrared Spectrometry (FTIR) was carried out on a PerkinElmer Spectrum 2000 FTIR with an attenuated total reflectance (ATR) crystal accessory (Golden Gate). The spectra were calculated by means of 16 individual scans at 2 $cm^{-1}$ resolution in the 4000-600 $cm^{-1}$ interval with corrections for atmospheric water and carbon dioxide.

Processing of Industrial Norway Spruce Chip Derived Hydrolyzates

Example 1

Extraction of Hemicelluloses from Industrial Norway Spruce Chips

Four 250 g batches of dried industrial chips, obtained from spruce (*Picea abies*) with a dry content of 95% and screened on a laboratory screen passing 8 mm but not 2 mm, was charged to batch autoclaves with 2 l of de-ionized water each. The mixture was processed at 160° C. for 60 min after which the wood chips were separated from the hydrolyzate on a paper machine filter (Monodur PA 71 µm, Derma AB). Each batch of chips was washed with 500 ml of boiling de-ionized water. The liquid fractions were combined, giving a total volume of 8.2 l. The hydrolyzate was further filtrated by micro filtration in a pilot scale ultrafiltration machine (Mini kerasep module, Novasep) with a ceramic membrane (The kerasep 0.45 µm, Novasep). Two liters of de-ionized water was added at the end of the filtration giving a 9 liter final volume of permeate (sample SCHW). The total yield of wood substances isolated with the hydrolyzate corresponded to 4.6%, calculated on dry wood chips.

Example 2

Upgrading of the Spruce Chip Hydrolyzate by Ultrafiltration

The hydrolyzate (SCHW) was upgraded by fractionation using ultrafiltration (Mini kerasep module, Novasep) employing a ceramic membrane with a cut-off of 1 kDa (The kerasep 1 kDa, Novasep). This was done to filter away the small molecular weight substances from the sample. The membrane filtration was performed to concentrate the retentate (the high molecular weight fraction) down to a volume of 2 l and thus giving 7 l permeate (the low molecular weight fraction). The high molecular weight fraction was further purified by diluting it with de-ionised water to 9 l and then again membrane filtering down to a volume of 2 l. The yield of high molecular weight materials thus obtained from the wood hydrolyzates by membrane filtration was 52% based on dry weight of the hydrolyzate. The sample is abbreviated as SCHW UF1.

Example 3

Polymerization of the Sample SCHW UF1

Upgraded hydrolyzate (sample, SCHW UF1) was treated with laccase-enzyme (NS51002, Novozymes Bagsvaerd, Denmark) under the following conditions: Enzyme dosage 14 U/g of hydrolyzate, hydrolyzate concentration 100 mg/ml, pH 5.0, temperature +40° C., reaction time 3 hours during which time pure oxygen gas was introduced to the sample. The treatment with these conditions gave the sample (SCHW UF1 P).

Example 4

Fractionation of the Polymerized Sample SCHW UF1 P

The sample subjected to polymerization was fractionated using ultrafiltration (Solvent-Resistant Stirred Cell, Millipore) employing a cellulose membrane with a molecular weight cut-off of 30 kDa (PLTK07610, Millipore). 1 volume of the sample was diluted with 9 volumes of de-ionized water to give a concentration of 10 g/l. The membrane filtration was performed to separate the retentate (the high molecular weight fraction, HMw) from the permeate (the small molecular weight fraction, sMw) by forcing the sample through the membrane in the ultrafiltration cell under nitrogen gas in a pressure of 3 bar with stirring. The ultrafiltration was employed until the volume of the retentate (abbreviated as SCHW UF1 P HMw) reached 1 volume from the starting volume of 10 giving thus a permeate (abbreviated as SCHW UF1 P sMw) volume of 9. The retentate was further purified by diluting the sample with one volume of de-ionized water and employing the ultrafiltration again until the volume of the retentate reached a volume of 1. The amount of dry matter in the fraction SCHW UF1 P HMw represented 23% and in the fraction SCHW UF1 P sMw 77% of the total dry matter amount.

Example 5

Upgrading of the Norway Spruce Hydrolyzate by Ethanol Precipitation

The sample (SCHW) was upgraded by ethanol precipitation. This was done to isolate the hemicelluloses from substances that are soluble in organic solvents. The hydrolyzate was concentrated by vacuum evaporation. The sample was then added to technical grade ethanol, the volume percentage of ethanol being at least 90, and the hemicelluloses were allowed to precipitate overnight in a cold room. The samples were centrifuged at 4000 g for 25 min. The precipitated hemicelluloses were collected and washed twice with 1 volume of ethanol and once with 1 volume of acetone. The precipitate was finally dried under vacuum and weighed giving the sample SCHW E.

Example 6

Polymerization of the Sample SCHW E

Upgraded hydrolyzate (sample, SCHW E) was treated with laccase-enzyme (NS51002, Novozymes Bagsvaerd, Denmark) under the following conditions: Enzyme dosage 14 U/g of hydrolyzate, pH 5.0, hydrolyzate concentration 100 mg/ml, temperature 40° C., reaction time 3 hours during which time pure oxygen gas was introduced to the sample. The treatment with these conditions gave the sample (SCHW EP).

Example 7

Film Preparation for Tensile Testing of the Sample SCHW UF1

An upgraded hydrolyzate (SCHW UF1) had been obtained according to examples 1 and 2 above, and thereafter freeze dried. The sample was dissolved in water in slightly elevated temperatures of 40-50° C. The sample was thereafter subjected to centrifugation (4000 g, 15 min) to remove a small amount of undissolved material. Polyethyleneimine (PEI, Lupasol® P, BASF) with a molecular weight of 750000 Da and glycerol was mixed into the polymer sample with ratios between SCHW UF1:PEI:glycerol being 3:1:1 counted as dry mass of the total mass of 400 mg. The dry matter concentration of the solution was 0.013 g/ml. The water solution was thereafter cast on a flat dish (9 cm*9 cm) that was covered with a thin film of teflon. The water was allowed to slowly evaporate at room temperature until it was completely dry, producing thin, transparent and dry film which was manually removed from the dish. The mechanical properties of the films were measured and they are presented in the table 3.

Example 8

Film Preparation for Tensile Testing of the Samples SCHW UF1 P sMw and SCHW UF1 P HMw A low and high molecular weight fraction of a polymerized and fractionated sample (SCHW UF1 P sMw and SCHW UF1 P HMw) had been obtained according to examples 1 to 4 above, and thereafter freeze dried. The sample was dissolved in water in slightly elevated temperatures of 40-50° C. The sample was thereafter subjected to centrifugation (4000 g, 15 min) to remove a small amount of undissolved material. Polyethyleneimine (PEI, Lupasol® P, BASF) with a molecular weight of 750000 Da and glycerol was mixed into the polymer sample with ratios between sample polymer:PEI:glycerol being 3:1:1 counted as dry mass of the to total mass of 400 mg. The dry matter concentration of the solution was 0.013 g/ml. The water solution was thereafter cast in a flat dish (9 cm*9 cm) that was covered with a thin film of teflon. The water was allowed to slowly evaporate at room temperature until it was completely dry, producing thin, transparent and dry films which were manually removed from the dishes. The mechanical properties of the films were measured and they are presented in the table 3.

TABLE 1

Chemical composition of the processed Norway spruce hydrolyzates, indicating that the samples consist mainly of a galactoglucomannan, but also an arabinglucuronoxylan.

| Sample | Composition (relative % of carbohydrates) | | | | | Composition (% of dry matter) | |
|---|---|---|---|---|---|---|---|
| | Arabi-nose | Xylose | Man-nose | Galac-tose | Glu-cose | Klason lignin | Ash |
| SCHW UF1 | 8.0 | 16.9 | 52.4 | 9.5 | 13.0 | 5.4 | 0.8 |
| SCHW UF1 P sMw | 9.4 | 17.5 | 50.2 | 10 | 12.9 | 0.5 | 2.3 |
| SCHW UF1 P HMw | 3.0 | 7.3 | 64.6 | 8.6 | 16.5 | 20.0 | 1.3 |

TABLE 2

Size exclusion chromatography results (molecular weight parameters) of the processed Norway spruce hydrolyzates.

| Sample | $M_n$ | $M_w$ | $M_w/M_n$ |
|---|---|---|---|
| SCHW UF1 | 7000 | 10400 | 1.5 |
| SCHW UF1 P | 8400 | 28100 | 2.2 |
| SCHW UF1 P sMw | 7400 | 10500 | 1.5 |
| SCHW UF1 P HMw | 23800 | 62700 | 2.6 |
| SCHW E | 5900 | 7700 | 1.3 |
| SCHW EP | 5500 | 12900 | 1.6 |

TABLE 3

Mechanical properties of the films made using the processed Norway spruce hydrolyzates (sample polymer:PEI:glycerol ratio 3:1:1) showing that the crosslinking treatment resulted in improved mechanical performance.

| Sample polymer | Stress at max. load (MPa) | Strain at break (%) | E-modulus (MPa) |
|---|---|---|---|
| SCHW UF1 | 4.2 | 13 | 64 |
| SCHW UF1 P sMw | 4.0 | 24 | 24 |
| SCHW UF1 P HMw | 9.8 | 9 | 240 |

The processing of industrial Eucalyptus chip derived hydrolyzates

Example 9

Extraction of Hemicelluloses from Industrial Eucalyptus Chips

A 250 g batch of dried industrial chips, obtained from Eucalyptus (*Eucalyptus urograndis*) with a dry content of 95% and screened on a laboratory screen passing 8 mm but not 2 mm, was charged to a batch autoclave with 2 l of de-ionised water. The mixture was processed at 150° C. for 60 min after which the wood chips were separated from the hydrolyzate on a paper machine filter (Monodur PA 71 μm, Derma AB). The chips were washed with 500 ml of boiling de-ionised water. The liquid fractions were combined, giving a total volume of ~2 l with pH of 3.5. The hydrolyzate was further filtrated in a büchner funnel with a cellulose membrane thus giving the sample EGCHW.

Example 10

Upgrading Of the Eucalyptus Hydrolyzate by Ethanol Precipitation

The hydrolyzate (EGCHW) was upgraded by ethanol precipitation. This was done to isolate the hemicelluloses from substances that are soluble in organic solvents. The hydrolyzate was concentrated by vacuum evaporation. The sample was then added to technical grade ethanol, the volume percentage of ethanol being at least 90, and the hemicelluloses were allowed to precipitate overnight in a cold room. The samples were centrifuged at 4000 g for 25 min The precipitated hemicelluloses were collected and washed twice with 1 volume of ethanol and once with 1 volume of acetone. The precipitate was finally dried under vacuum and weighed giving the sample EGCHW E.

Example 11

Polymerization of the Sample EGCHW E

Upgraded hydrolyzate (sample, EGCHW E) was treated with laccase-enzyme (NS51002, Novozymes Bagsvaerd, Denmark) under the following conditions: Enzyme dosage 14 U/g of hydrolyzate, pH 5.0, hydrolyzate concentration 100 mg/ml, temperature 40° C., reaction time 3 hours during which time pure oxygen gas was introduced to the sample. The treatment with these conditions gave the sample (EGCHW EP).

TABLE 4

Chemical composition of the processed *Eucalyptus* hydrolyzates indicating that the sample consists mostly of a glucuronoxylan but also of a glucomannan.

| Sample | Composition (relative % of carbohydrates) | | | | | Composition (% of dry matter) | |
|---|---|---|---|---|---|---|---|
| | Arabi-nose | Xylose | Man-nose | Galac-tose | Glu-cose | Klason lignin | Ash |
| EGHW E | 2.3 | 51.3 | 8.2 | 19.3 | 19.0 | 9.8 | 11.6 |

TABLE 5

Size exclusion chromatography results (molecular weight parameters) of the processed Eucalyptus hydrolyzates

| Sample | $M_n$ | $M_w$ | $M_w/M_n$ |
|---|---|---|---|
| EGCHW E | 7300 | 12600 | 1.7 |
| EGCHW EP | 10700 | 57100 | 5.3 |

Example 12

Extraction of the Hemicelluloses from the Process Waters of Thermomechanical Pulping 60 liters of process waters from thermomechanical pulping process of Norway spruce (*Picea abies*) was taken from the process stream. The sample was filtrated by micro filtration in a pilot scale ultrafiltration machine (Mini kerasep module, Novasep) with a 0.45 μm ceramic membrane (The kerasep 0.45 μm, Novasep). Two liters of de-ionized water was added at the end of the filtration giving a 58 liter final volume of permeate (sample TMP).

Example 13

Upgrading of the TMP Process Water Hydrolyzate by Ultrafiltration 10 l of the sample (IMP) was upgraded by fractionation using ultrafiltration (Mini Kerasep module, Novasep) employing a ceramic membrane with a cutoff of either 1 or 5 kDa (The Kerasep, Novasep). This was done to filter away the small molecular weight substances from the sample. The membrane filtration was performed to concentrate the retentate (the high molecular weight fraction) down to a volume of 2 l and thus giving 7 l permeate (the low molecular weight fraction). The high molecular weight fraction was further purified by diluting it with de-ionised water to 9 l and then again membrane filtering down to a volume of 2 l. The yield of high molecular weight materials thus obtained from the wood hydrolyzates by membrane filtration was 53.2% and 44.6% respectively to the membranes used (1 or 5 kDa). These samples are abbreviated as TMP UF1 and TMP UF5 respectively to the membrane cutoff (1 or 5 kDa).

Example 14

Polymerization of the sample TMP UF1

Upgraded hydrolyzate (sample, TMP UF1) was treated with laccase-enzyme (NS51002, Novozymes Bagsvaerd, Denmark) under the following conditions: Enzyme dosage 14 U/g of hydrolyzate, pH 5.0, hydrolyzate concentration 100 mg/ml, temperature 40° C., reaction time 3 hours during which time pure oxygen gas was introduced to the sample. The treatment with these conditions gave the sample (TMP UF1 P).

Example 15

Fractionation of the Polymerized Sample TMP UF1 P

The sample subjected to polymerization was fractionated using ultrafiltration (Solvent-Resistant Stirred Cell, Millipore) employing a cellulose membrane with a molecular weight cutoff of 30 kDa (PLTK07610, Millipore). 1 volumes of the sample was diluted with 9 volumes of de-ionised water to give a concentration of 10 g/l. The membrane filtration was performed to separate the retentate (the high molecular weight fraction, HMw) from the permeate (the small molecular weight fraction, sMw) by forcing the sample through the membrane in the ultrafiltration cell under nitrogen gas in a pressure of 3 bar with stirring. The ultrafiltration was employed until the volume of the retentate (abbreviated as TMP UF1 P HMw) reached 1 volume from the starting volume of 10 giving thus a permeate (abbreviated as TMP UF1 P sMw) volume of 9. The retentate was further purified by diluting the sample with one volume of de-ionized water and employing the ultrafiltration again until the volume of the retentate reached a volume of 1. The amount of dry matter in the fraction TMP UF1 P HMw represented 50% and in the fraction TMP UF1 P sMw 50% of the total dry matter amount.

Example 16

Film preparation for tensile testing of the sample TMP UF1

An upgraded hydrolyzate (TMP UF1) had been obtained according to examples 15 and 16 above, and thereafter freeze dried. The sample was dissolved in water in slightly elevated temperatures of 40-50° C. The sample was thereafter subjected to centrifugation (4000 g, 15 min) to remove a small amount of undissolved material. Polyethyleneimine (PEI, Lupasol® P, BASF) with a molecular weight of 750000 Da and glycerol was mixed into the polymer sample with ratios between TMP UF1:PEI:glycerol being 7:2:2 counted as dry mass. The dry matter concentration of the solution was 0.013 g/ml. The water solution was thereafter cast in a flat dish (9 cm*9 cm) that was covered with a thin film of teflon. The water was allowed to slowly evaporate at room temperature until it was completely dry, producing thin, transparent and dry films which were manually removed from the dishes. The mechanical properties of the films were measured and they are presented in the table 10.

Example 17

Film Preparation for Tensile Testing of the Samples TMP UF1 P sMw and TMP UF1 P HMw A low and high molecular weight fraction of polymerized and fractionated samples (TMP UF1 P sMw and TMP UF1 P HMw) had been obtained according to examples 1 to 4 above, and thereafter freeze dried. The sample was dissolved in water in slightly elevated temperatures of 40-50° C. The sample was thereafter subjected to centrifugation (4000 g, 15 min) to remove a small amount of undissolved material. Polyethyleneimine (PEI, Lupasol® P, BASF) with a molecular weight of 750000 Da and glycerol was mixed into the polymer sample with ratios between sample polymer:PEI:glycerol being 7:2:2 counted as dry mass. The dry matter concentration of the solution was 0.013 g/ml. The water solution was thereafter cast in a flat dish (9 cm*9 cm) that was covered with a thin film of teflon. The water was allowed to slowly evaporate at room temperature until it was completely dry, producing thin, transparent and dry films which were manually removed from the dishes. The mechanical properties of the films were measured and they are presented in the table 10.

Example 18

Film preparation for tensile testing of the sample TMP UF1 P HMw

A high molecular weight fraction of a polymerized and fractionated sample (TMP UF1 P HMw) had been obtained according to examples 1 to 4 above, and thereafter freeze dried. The sample was dissolved in water in slightly elevated temperatures of 40-50° C. The sample was thereafter subjected to centrifugation (4000 g, 15 min) to remove a small amount of undissolved material. Polyethyleneimine (PEI, Lupasol® P, BASF) with a molecular weight of 750000 Da and glycerol was mixed into the polymer sample with ratios between sample polymer:PEI:glycerol being 7:2:1 counted as dry mass. The dry matter concentration of the solution was 0.013 g/ml. The water solution was thereafter cast in a flat dish (9 cm*9 cm) that was covered with a thin film of teflon. The water was allowed to slowly evaporate at room temperature until it was completely dry, producing thin, transparent and dry films which were manually removed from the dishes. The mechanical properties of the films were measured and they are presented in the table 11.

Example 19

Polymerization of the Sample TMP UF5

Upgraded hydrolyzate that was obtained according to the examples 15 and 16 (sample TMP UF5) was treated with laccase-enzyme (NS51002, Novozymes Bagsvaerd, Denmark) under the following conditions: Enzyme dosage 14 U/g of hydrolyzate, pH 5.0, hydrolyzate concentration 100 mg/ml, temperature 40° C., reaction time 3 hours during which time pure oxygen gas was introduced to the sample. The treatment with these conditions gave the sample (TMP UF5 P).

Example 20

Fractionation of the Polymerized Sample TMP UF5 P

The sample subjected to polymerization (sample TMP UF5 P) was fractionated using ultrafiltration (Solvent-Resistant Stirred Cell, Millipore) employing a cellulose membrane with a molecular weight cut-off of 30 kDa (PLTK07610, Millipore). 1 volumes of the sample was diluted with 9 volumes of de-ionised water to give a concentration of 10 g/l. The membrane filtration was performed to separate the retentate (the high molecular weight fraction, HMw) from the permeate (the small molecular weight fraction, sMw) by forcing the sample through the membrane in the ultrafiltration cell under nitrogen gas in a pressure of 3 bar with stirring. The ultrafiltration was employed until the volume of the retentate (abbreviated as TMP UF5 P HMw) reached 1 volume from the starting volume of 10 giving thus a permeate (abbreviated as TMP UF5 P sMw) volume of 9. The retentate was further purified by diluting the sample with one volume of de-ionized water and employing the ultrafiltration again until the volume of the retentate reached a volume of 1. The amount of dry matter in the fraction TMP UF5 P HMw represented 56% and in the fraction TMP UF5 P sMw 44% of the total dry matter amount.

Example 21

Film Preparation for Tensile and Oxygen Barrier Testing of the Sample TMP UF5 P HMw A high molecular weight fraction of a polymerized and fractionated sample (TMP UF5 P HMw) had been obtained according to examples 15-16 and 22-23 above, and thereafter freeze dried. The sample was dissolved in water in slightly elevated temperatures of 40-50° C. The sample was thereafter subjected to centrifugation (4000 g, 15 min) to remove a small amount of undissolved material. Polyethyleneimine (PEI, Lupasol® P, BASF) with a molecular weight of 750000 Da and glycerol was mixed into the polymer sample with ratios between sample polymer:PEI:glycerol being 7:2:1 counted as dry mass. The dry matter concentration of the solution was 0.013 g/ml. The water solution was thereafter cast in a flat dish (9 cm*9 cm) that was covered with a thin film of teflon. The water was allowed to slowly evaporate at room temperature until it was completely dry, producing thin, transparent and dry films which were manually removed from the dishes. The mechanical properties of the film were measured and they are presented in the table 12. The measured oxygen transmission rate of the film (with the average thickness of 80 μm) in 50% RH was below 0.008 cm$^3$/(m2*24 h) indicating good oxygen barrier properties.

Example 22

Upgrading of the TMP Process Water by Ethanol Precipitation

The sample that was obtained according to the example 15 (sample TMP) was upgraded by ethanol precipitation. This was done to isolate the hemicelluloses from substances that are soluble in organic solvents. The hydrolyzate was concentrated by vacuum evaporation. The sample was then added to technical grade ethanol, the volume percentage of ethanol being at least 90, and the hemicelluloses were allowed to precipitate overnight in a cold room. The samples were centrifuged at 4000 g for 25 min. The precipitated hemicelluloses were collected and washed twice with 1 volume of ethanol and once with 1 volume of acetone. The precipitate was finally dried under vacuum and weighed giving the sample TMP E.

Example 23

Polymerization of the Sample TMP E

Upgraded hydrolyzate that was obtained according to the example 15 and 25 (sample, TMP E) was treated with laccase-enzyme (NS51002, Novozymes Bagsvaerd, Denmark) under the following conditions: Enzyme dosage 14 U/g of hydrolyzate, pH 5.0, hydrolyzate concentration 100 mg/ml, temperature 40° C., reaction time 3 hours during which time pure oxygen gas was introduced to the sample. The treatment with these conditions gave the sample (TMP E P).

TABLE 8

The chemical composition of the processed hydrolyzates derived from thermomechanical pulping of Norway spruce, indicating that the samples consists mainly of a galactoglucomannan but also of an arabinoglucuronoxylan.

| Sample | Composition (relative % of carbohydrates) | | | | | Composition (% of dry matter) | |
|---|---|---|---|---|---|---|---|
| | Arabinose | Xylose | Mannose | Galactose | Glucose | Klason lignin | Ash |
| TMPUF1 | 3.9 | 2.1 | 63.3 | 13.8 | 16.9 | 15.1 | 8.5 |
| TMP UF1 P sMw | 3.2 | 2.2 | 65.5 | 11.2 | 18.0 | 3.2 | 10.1 |
| TMP UF1 P HMw | 5.6 | 2.7 | 57.8 | 17.8 | 16.1 | 41.6 | 6.2 |
| TMP UF5 | 3.4 | 2.4 | 64.6 | 13.1 | 16.8 | 16.0 | 8.5 |
| TMP UF5 P sMw | 3.1 | 1.7 | 64.8 | 9.3 | 21.2 | 4.0 | 10.1 |
| TMP UF5 P HMw | 6.1 | 3.6 | 56.3 | 18.5 | 15.5 | 27.0 | 6.2 |

TABLE 9

Size exclusion chromatography results (molecular weight parameters) of the processed hydrolyzates derived from thermomechanical pulping of Norway spruce

| Sample | $M_n$ | $M_w$ | $M_w/M_n$ |
|---|---|---|---|
| TMP UF1 | 11300 | 17600 | 1.6 |
| TMP UF1 P | 15100 | 37600 | 2.5 |
| TMP UF1 P sMw | 10000 | 14500 | 1.4 |
| TMP UF1 P HMw | 27100 | 59500 | 2.2 |
| TMP UF5 | 14800 | 22400 | 1.5 |
| TMP UF5 P | 16200 | 32900 | 2.0 |
| TMP UF5 P sMw | 9700 | 13600 | 1.4 |
| TMP UF5 P HMw | 20500 | 40000 | 1.9 |

TABLE 10

Mechanical properties of the films made using the processed Norway spruce hydrolyzates (sample polymer:PEI:glycerol ratio 3:1:1) showing that the crosslinking treatment resulted in improved mechanical performance.

| Sample polymer | Stress at max. load (MPa) | Strain at break (%) | E-modulus (MPa) |
|---|---|---|---|
| TMP UF1 | 2.2 | 23 | 10 |
| TMP UF1 P sMw | 1.6 | 27 | 6 |
| TMP UF1 P HMw | 8.0 | 21 | 98 |

TABLE 11

Mechanical properties of the films made using the processed Norway spruce hydrolyzates (sample polymer:PEI:glycerol ratio 7:2:1). The samples TMP UF1 and TMP UF1 P sMw gave brittle films that were not possible to use for measurements indicating that the crosslinking had a positive effect on the mechanical performance of the film.

| Sample polymer | Stress at max. load (MPa) | Strain at break (%) | E-modulus (MPa) |
|---|---|---|---|
| TMP UF1 | N/A | N/A | N/A |
| TMP UF1 P sMw | N/A | N/A | N/A |
| TMP UF1 P HMw | 15.0 | 6 | 400 |

TABLE 12

Mechanical properties of the films made using the processed Norway spruce hydrolyzates (sample polymer:PEI:glycerol ratio 7:2:1). The samples TMP UF5 and TMP UF5 P sMw gave brittle films that that were not possible to use for measurements indicating that the crosslinking had a positive effect on the mechanical performance of the film.

| Sample polymer | Stress at max. load (MPa) | Strain at break (%) | E-modulus (MPa) |
|---|---|---|---|
| TMP UF5 | N/A | N/A | N/A |
| TMP UF5 P sMw | N/A | N/A | N/A |
| TMP UF5 P HMw | 33.8 | 3.3 | 1900 |

Example 24

Polymerization of the Sample TMP UF5 by Horseradish Peroxidase Enzyme

Upgraded hydrolyzate that was obtained according to the examples 15 and 16 (sample TMP UF5) was dissolved in 20 mM sodium phosphate buffer with pH 6.0 and treated with horseradish peroxidase-enzyme (P8375, Sigma-Aldrich) under the following conditions: enzyme dosage 13 U/g of hydrolyzate, temperature 23° C., hydrolyzate concentration 100 mg/ml, reaction time 30 min. The reaction was started by adding 5.2 µmol of hydrogen peroxide ($H_2O_2$, cat.: 21,676-3, Sigma-Aldrich) to the solution. The treatment with these conditions gave the sample TMP UF5 HRP.

Example 25

Investigation of Laccase Polymerization Parameters

Upgraded hydrolyzate (sample, SCHW UF1) was dissolved in four separate vials to a hydrolyzate concentration of 100 mg/ml. Dosages of laccase-enzyme NS51002 (activity units per g of hydrolyzate) was added to the four vials as follows: 0.014 U/g, 0.14 U/g, 1.4 U/g and 14 U/g. Temperature was set to 40° C., pH adjusted to 5 and reaction was started as pure oxygen gas was introduced to the four samples. Sample aliquots were collected from the vial where 14 U/g NS51002 was added after 15, 30, 60, 120 and 240 minutes of oxidation for size chromatography analysis. The content in the retraining vials, 0.014 U/g, 0.14 U/g and 1.4 U/g were analyzed after 240 minutes. The treatment with these conditions gave the samples SCHW UF1 14 U 15 min, SCHW UF1 14 U 30 min, SCHW UF1 14 U 60 min, SCHW UF1 14 U 120 min, SCHW UF1 14 U 240 min, SCHW UF1 1.4 U 240 min SCHW UF1 0.14 U 240 min and SCHW UF1 0.014 U 240 min. The size exclusion chromatography results of these samples are given in the table 13.

TABLE 13

Size exclusion chromatography results (molecular weight parameters) of polymerization of hydrolyzate SCHW 1 UF1 at various times and added laccase concentrations.

| Sample | $M_n$ | $M_w$ | $M_w/M_n$ |
|---|---|---|---|
| SCHW UF1 | 7000 | 10400 | 1.4 |
| SCHW UF1 14U 15 min | 13500 | 29100 | 2.2 |
| SCHW UF1 14U 30 min | 13800 | 31600 | 2.3 |
| SCHW UF1 14U 60 min | 13700 | 33600 | 2.5 |
| SCHW UF1 14U 120 min | 14000 | 34400 | 2.5 |
| SCHW UF1 14U 240 min | 13700 | 34400 | 2.5 |
| SCHW UF1 1.4U 240 min | 13100 | 32300 | 2.5 |
| SCHW UF1 0.14U 240 min | 10907 | 29000 | 2.4 |
| SCHW UF1 0.014U 240 min | 10700 | 28000 | 2.2 |

Example 26

Polymerization of the Sample TMP UF5 with Different Laccase-Enzymes

The upgraded hydrolyzate that was obtained according to the examples 15 and 16 (sample TMP UF5) was treated with two different laccase-enzymes NS51003 (Novozymes Bagsvaerd, Denmark) and 53739 (Sigma 53739, Sigma-Aldrich), under the following conditions: enzyme dosage 14 U/g of hydrolyzate, temperature 40° C., pH 7 for the enzyme NS51003 and pH 4.5 for the enzyme 53739, hydrolyzate concentration 100 mg/ml, reaction time 3 hours during which time pure oxygen gas was introduced to the sample. The treatment with these conditions gave the samples TMP UF5 NS51003 and TMP UF5 Sigma 53739.

TABLE 14

Size exclusion chromatography results (molecular weight parameters) of polymerization of hydrolyzate TMP UF5 with different laccase-enzymes.

| Sample | $M_n$ | $M_w$ | $M_w/M_n$ |
|---|---|---|---|
| TMP UF5 | 11300 | 17600 | 1.6 |
| TMP UF5 NS51003 | 12600 | 22000 | 1.9 |
| TMP UF5 Sigma 53700 | 17100 | 34200 | 2.0 |

Example 27

Polymerization of the Sample TMP UF5 by Immobilized Laccase-enzyme

Laccase-enzyme (NS51002, Novozymes Bagsvaerd, Denmark) was immobilized on controlled porosity carrier (CPC) silica beads using the GlUTAL/APlES covalent immobilization technique. An amount of 4 g of CPC silica beads (0.4-0.5 mm average particle size, 375 Å pore diameter and a surface area of 42.1 $m^2/g$) were activated at room temperature for 2 hours under vacuum with degassed 2.5% (v/v) glutaraldehyde in 0.1 M acetate buffer at pH 5. After the activation, the beads were washed twice with acetate buffer and laccase was added (700 U in 0.1M acetate buffer, pH 5). Immobilisation took place at 4° C. for 48 h after which the beads were washed in de-ionized water and acetate buffer until no laccase activity could be detected in the washing liquid.

The amount of protein in the supernatant solution before and after immobilisation was determined through the Bradford method with BSA as standard. Bound protein was determined as the difference between initial and final protein concentrations.

The immobilized laccase was loaded into a tubular packed bed reactor (ID.=2 cm, h=3.5 cm, Vbed=12 ml, Vvoid=2.5 ml). The upgraded hydrolyzate that was obtained according to the examples 15 and 16 (sample TMP UF5) process water was continuously recirculated at 3.5 ml/min through the column from a reservoir under constant oxygen saturation. The recirculation proceeded for 3 hours after which the oxidation reaction was aborted. The treatment with these conditions gave the sample TMP UF5 IL

TABLE 15

Size exclusion chromatography results (molecular weight parameters) of the polymerization of hydrolyzates derived from thermomechanical pulping of Norway spruce with immobilized laccase

| Sample | Mn | Mw | $M_w/M_n$ |
|---|---|---|---|
| TMP UF5 | 15000 | 22800 | 1.5 |
| TMP UF5 IL | 16900 | 30500 | 1.8 |

Example 28

Polymerization of a Mixture of Hemicelluloses with Bound Aromatic Moieties into a Hybrid Hemicellulose A mixture of an upgraded hydrolyzate from the thermomechanical pulping process liquids of Norway spruce that was obtained according to the examples 15 and 16 (sample, TMP UF5) and an upgraded hydrolyzate from the hydro thermal treatment of Eucalyptus that was obtained according to the examples 9 and 10 (sample, EGHW E) was treated with laccase-enzyme (NS51002, Novozymes Bagsvaerd, Denmark) under the following conditions: Enzyme dosage 14 U/g of hydrolyzate, pH 5.0, hydrolyzate concentration of each sample 50 mg/ml, temperature 40° C., reaction time 3 hours during which time pure oxygen gas was introduced to the sample. The sample was thereafter subjected to centrifugation (4000 g, 15 min) to remove undissolved material. The treatment with these conditions gave the sample (TMP UF5-EGHW EH).

Example 29

Isolation of a Hybrid Hemicellulose from a Hydrolyzate Mixture by Ultrafiltration The sample subjected to polymerization (sample TMP UF5-EGHW E H) was fractionated using ultrafiltration (Solvent-Resistant Stirred Cell, Millipore) employing a cellulose membrane with a molecular weight cut-off of 30 kDa (PLTK07610, Millipore). 1 volumes of the sample was diluted with 9 volumes of de-ionised water to give a concentration of 10 g/l. The membrane filtration was performed to separate the retentate (the high molecular weight fraction, HMw) from the permeate (the small molecular weight fraction, sMw) by forcing the sample through the membrane in the ultrafiltration cell under nitrogen gas in a pressure of 3 bar with stirring. The ultrafiltration was employed until the volume of the retentate (abbreviated as TMP UF5-EGHW EH HMw) reached 1 volume from the starting volume of 10 giving thus a permeate (abbreviated as TMP UF5—EGHW EH sMw) volume of 9. The retentate was further purified by diluting the sample with one volume of de-ionized water and employing the ultrafiltration again until the volume of the retentate reached a volume of 1. The amount of dry matter in the fraction TMP UF5-EGHW EH HMw represented 35% and in the fraction TMP UF5-EGHW EH sMw 65% of the total dry matter amount

TABLE 16

The chemical composition of the hybrid and the small molecular weight fraction, indicating that the samples consist of mixtures of galactoglucomannans, glucuronoxylans and arabinoxylans.

| | Composition (relative % of carbohydrates) | | | | | Composition (% of dry matter) | |
|---|---|---|---|---|---|---|---|
| Sample | Arabinose | Xylose | Mannose | Galactose | Glucose | Klason lignin | Ash |
| TMP UF5 - EGHW EH sMw | 2.1 | 14.1 | 44.7 | 16.2 | 22.2 | 2.7 | 12.8 |
| TMP UF5 - EGHW EH HMw | 1.8 | 7.8 | 51.7 | 14.5 | 24.2 | 15.5 | 2.5 |

TABLE 17

Size exclusion chromatography results (molecular weight parameters) of the hybrid and the small molecular weight fraction

| Sample | $M_n$ | $M_w$ | $M_w/M_n$ |
|---|---|---|---|
| TMP UF5 - EGHW E reference | 15800 | 24300 | 1.5 |
| TMP UF5 - EGHW EP | 15000 | 38200 | 2.5 |
| TMP UF5 - EGHW EH sMw | 10600 | 15200 | 1.4 |
| TMP UF5 - EGHW EH HMw | 26600 | 59100 | 2.2 |

Example 30

Upgrading of the CTMP Process Water Sample by Ultrafiltration 2 l of process waters from a chemitermomechanical pulping process (CTMP) of Norway spruce (*Picea abies*) was taken from the process stream of a Swedish mill. The fibrous material was separated from the hydrolyzate on a paper machine filter (Monodur PA 71 µm, Derma AB) and the hydrolyzate was further filtrated in a büchner funnel with a cellulose membrane thus giving the sample abbreviated as CTMP. The dry matter content of the sample was 3 g/l. The sample was upgraded by using ultrafiltration (Solvent-Resistant Stirred Cell, Millipore) employing a cellulose membrane with a molecular weight cut-off of 5 kDa (PLCC07610, Millipore). This was done to filter away the small molecular weight substances from the sample. The membrane filtration was performed in 350 ml batches by forcing the sample through the membrane in the ultrafiltration cell under nitrogen gas in a pressure of 3 bar with stirring. The retentate (the high molecular weight fraction) was concentrated to a volume of 400 ml and thus giving 1.6 l permeate (the low molecular weight fraction). The retentate was further purified by diluting it with de-ionised water to 800 ml and then again concentrating the sample to a volume of 400 ml. The yield of high molecular weight material thus obtained from the process waters by membrane filtration was 19% (sample CTMP UF5).

Example 31

Polymerization of the Sample CTMP UF5

Upgraded process water sample (sample, CTMP UF5) was treated with laccase-enzyme (NS51002, Novozymes Bagsvaerd, Denmark) under the following conditions: Enzyme dosage 14 U/g of hydrolyzate, pH 5.0, hydrolyzate concentration 100 mg/ml, temperature 40° C., reaction time 3 hours during which time pure oxygen gas was introduced to the sample. The treatment with these conditions resulted in the sample CTMP UF5 P.

Example 32

Fractionation of the Polymerized Sample CTMP UF5 P

The sample subjected to polymerization was fractionated using ultrafiltration (Solvent-Resistant Stirred Cell, Millipore) employing a cellulose membrane with a molecular weight cut-off of 30 kDa (PLTK07610, Millipore). 1 volume of the sample was diluted with 9 volumes of de-ionized water to give a concentration of 10 g/l. The membrane filtration was performed to separate the retentate (the high molecular weight fraction, HMw) from the permeate (the small molecular weight fraction, sMw) by forcing the sample through the membrane in the ultrafiltration cell under nitrogen gas in a pressure of 3 bar with stirring. The ultrafiltration was employed until the volume of the retentate (abbreviated as CTMP UF5 P HMw) reached 1 volume from the starting volume of 10 giving thus a permeate (abbreviated as CTMP UF5 P sMw) volume of 9. The retentate was further purified by diluting the sample with one volume of de-ionized water and employing the ultrafiltration again until the volume of the retentate reached a volume of 1. The amount of dry matter in the fraction CTMP UF5 P HMw represented 50% and in the fraction CTMP UF5 P sMw 50% of the total dry matter amount.

Example 33

Film Preparation for Tensile and Oxygen Barrier Testing of the Sample CTMP UF5 P HMw Samples CTMP UF5, CTMP UF5 sMw and CTMP UF5 P HMw had been obtained according to examples above, and thereafter freeze dried. Each sample was dissolved in water in 50° C. in a water bath. The sample was thereafter subjected to centrifugation (4000 g, 15 mm) to remove a small amount of undissolved material. Carboxymethyl cellulose (CMC, Carboxymethyl cellulose sodium salt, low viscosity, 21900, Huka Chemie AG, Buchs, Switzerland) was mixed into the polymer sample with ratios between sample polymer:CMC being 4:1 counted as dry mass. The dry matter concentration of the solution was 0.013 g/ml. The water solution was thereafter cast in a flat dish (9 cm*9 cm) that was covered with a thin film of teflon. The water was allowed to slowly evaporate at room temperature until it was completely dry, producing thin, transparent and dry films which were manually removed from the dishes. The mechanical properties of the films were measured and they are presented in the table 20. The measured oxygen transmission rate of the film (with an average thickness of 81 µm) prepared with the sample CTMP UF5 P HMw in 50% RH was 10 $cm^3/(m2*24\ h)$ indicating good oxygen barrier properties.

TABLE 18

The chemical composition of the processed hydrolyzates derived from chemithermomechanical pulping of Norway spruce, indicating that the samples consists of a galactoglucomannan.

| Sample | Composition (relative % of carbohydrates) | | | | | Composition (% of dry matter) | |
|---|---|---|---|---|---|---|---|
| | Arabinose | Xylose | Mannose | Galactose | Glucose | Klason lignin | Ash |
| CTMP UF5 | N/D | N/D | 61.0 | 7.0 | 32.0 | 10.9 | 10.5 |
| CTMP UF5 P sMw | N/D | N/D | 62.0 | 9.0 | 29.0 | N/A | N/A |
| CTMP UF5 P HMw | N/D | N/D | 60.0 | 34.0 | 6.0 | N/A | N/A |

TABLE 19

Size exclusion chromatography results (molecular weight parameters) of the processed hydrolyzates derived from chemithermomechanical pulping of Norway spruce

| Sample | $M_n$ | $M_w$ | $M_w/M_n$ |
|---|---|---|---|
| CTMP UF5 | 9700 | 14000 | 1.5 |
| CTMP UF5 P | 12200 | 32000 | 2.6 |
| CTMP UF5 P sMw | 9400 | 13200 | 1.4 |
| CTMP UF5 P HMw | 34300 | 64300 | 1.9 |

TABLE 20

Mechanical properties of the films made using the processed CTMP hydrolyzates (sample polymer:CMC ratio 4:1) The samples CTMP UF5 and CTMP UF5 P sMw gave low strenght films that were not possible to use for measurements indicating that the crosslinking had a positive effect on the mechanical performance of the film.

| Sample polymer | Stress at max. load (MPa) | Strain at break (%) | E-modulus (MPa) |
|---|---|---|---|
| CTMP UF1 | N/A | N/A | N/A |
| CTMP UF5 P sMw | N/A | N/A | N/A |
| CTMP UF5 P HMw | 44.0 | 2.8 | 1950 |

Example 34

Partial Acetylation of the Sample TMP UF5 P HMw 700 mg of the sample TMP UF5 P HMw was dissolved in 7 ml de-ionized water and 7 ml imidazole (1-methyl imidazole, 336092-100ML, Sigma-Aldrich, St Louis, USA) was added to the solution. The sample was put into a cold water bath and acetylation was started by adding 3.5 ml acetic anhydride (Acetic anhydride, 45840, Fluka/Sigma-Aldrich, Steinheim, Switzerland) to the solution. The sample was incubated for 10 minutes in these conditions. The acetylation reaction was terminated by adding 100 ml with de-ionized water to the solution. The acetylated sample was purified by ultrafiltration (Solvent-Resistant Stirred Cell, Millipore) employing a cellulose membrane with a molecular weight cut-off of 5 kDa (PLCC07610, Millipore). The membrane filtration was performed to separate the acetylation chemicals from the sample polymer (retentate) by forcing the sample through the membrane in the ultrafiltration cell under nitrogen gas in a pressure of 3 bar with stirring. The ultrafiltration was employed until the volume of the retentate (abbreviated as CTMP UF5 P HMw) reached 1 volume from the starting volume of 10 giving thus a permeate volume of 9. The retentate was further purified by diluting the sample with two volumes of de-ionized water and employing the ultrafiltration again until the volume of the retentate reached a volume of 1 resulting to the sample TMP UF5 P HMw A Example 35

Film Preparation of the Acetylated Sample TMP UF5 P HMw A

Sample TMP UF5 P HMw A had been obtained according to examples above, and thereafter freeze dried. The sample was dissolved in water in +50° C. in a water bath together with un-acetylated sample TMP UF5 P HMw and CMC (CMC, Carboxymethyl cellulose sodium salt, low viscosity, 21900, Huka Chemie AG, Buchs, Switzerland) with sample ratios being 3:6:1 (TMP UF5 P HMw A: TMP UF5 P HMw:CMC). Another film was made in a same way by mixing the un-acetylated sample TMP UF5 P HMw with CMC in ratios 7:3. The samples were thereafter subjected to centrifugation (4000 g, 15 min) to remove a small amount of undissolved material. The dry matter concentration of the solutions were 0.013 g/ml. The water solution was thereafter cast in a flat dish (9 cm*9 cm) that was covered with a thin film of teflon. The water was allowed to slowly evaporate at room temperature until it was completely dry, producing thin, transparent and dry films which were manually removed from the dishes. The amount of acetyl groups resulting the acetylation were measured by using FTIR and a comparison with the un-acetylated sample was made. The result is given in FIG. 2 indicating a successful acetylation.

Figure 2:
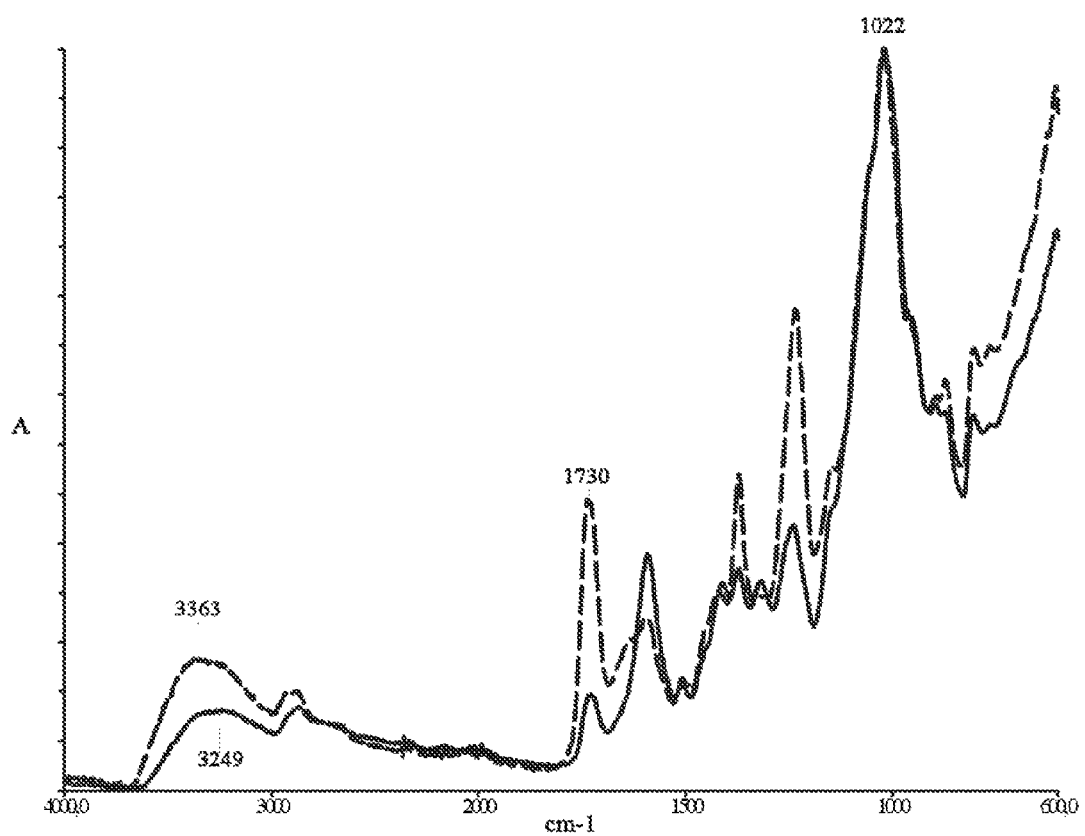
FIG. 2 shows an FTIR spectra from an experiment according to the invention.

FIG. 2 shows FTIR spectra (normalized to the hemicellulose main chain C-O stretching at 1022 $cm^{-1}$) of the films indicating that the sample containing the acetylated polymer (TMP UF5 P HMw A, dotted line) gives rise to a significantly higher peak at 1730 $cm^{-1}$ than the unacetylated sample (solid line) stemming from the acetylated pendant groups of the hemicellulose chains. This indicates a successful acetylation.

The invention claimed is:

1. A method for increasing the molecular weight of hemicellulose, selected from the group consisting of mannan and xylan, said method comprising the steps:
    a) obtaining at least one hemicellulose from wood, wherein the hemicellulose is selected from the group consisting of mannan and xylan, and at least a fraction of said hemicellulose comprising at least one bound aromatic group,
    b) subjecting the hemicellulose to oxidizing conditions to convert at least a fraction of said at least one bound aromatic group into radicals and reacting said radicals with each other to obtain hemicellulose with increased molecular weight, wherein the oxidation is achieved by adding an enzyme to the hemicellulose, wherein the enzyme is one selected from the group consisting of an oxidoreductase, an oxidoreductase with oxygen as acceptor, and laccase, and thereafter subjecting the resulting compounds to a separation with respect to molecular weight and thereby separating hemicellulose comprising bound aromatic groups from hemicelluloses without bound aromatic groups.

2. The method according to claim 1, wherein said hemicellulose is at least one hemicellulose selected from the group consisting of arabinoglucuronoxylan, glucuronoxylan, glucomannan and galactoglucomannan.

3. The method according to claim 1, wherein said at least one bound aromatic group is lignin.

4. The method according to claim 1, wherein the hemicellulose comprising at least one bound aromatic group is provided by hydrothermal treatment of wood.

5. The method according to claim 1, wherein molecules with a molecular weight lower than 1000 to 15000 Da are removed from the hemicellulose before step a).

6. The method according to claim 1, wherein the pH is adjusted to a value in the range from 3 to 10 before step a).

7. The method according to claim 1, wherein oxygen is added to the hemicellulose.

8. The method according to claim 1, wherein the enzyme is added at a temperature that is in the range from 20° C. to 80° C.

9. The method according to claim 1, wherein the resulting complexes of hemicelluloses with increased molecular weight are subjected to a derivatization, and wherein the derivatization is acetylation.

10. A barrier film comprising a hemicellulose manufactured according to claim 1.

* * * * *